(12) United States Patent
Caples et al.

(10) Patent No.: US 9,629,982 B2
(45) Date of Patent: *Apr. 25, 2017

(54) MEDICAL DEVICE CONTROL HANDLE WITH MULTIPLE PULLER WIRES

(71) Applicant: BIOSENSE WEBSTER (ISRAEL) LTD., Yokneam (IL)

(72) Inventors: Dennis C. Caples, Placentia, CA (US); Keshava Datta, Chino Hills, CA (US); Rajesh Pendekanti, Chino Hills, CA (US)

(73) Assignee: BIOSENSE WEBSTER (ISRAEL), LTD., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/848,770

(22) Filed: Sep. 9, 2015

(65) Prior Publication Data
US 2016/0045711 A1    Feb. 18, 2016

Related U.S. Application Data

(62) Division of application No. 13/341,840, filed on Dec. 30, 2011, now Pat. No. 9,162,036.

(51) Int. Cl.
*A61M 25/01* (2006.01)
*A61B 18/14* (2006.01)
(Continued)

(52) U.S. Cl.
CPC ......... *A61M 25/0136* (2013.01); *A61B 5/042* (2013.01); *A61B 5/6857* (2013.01);
(Continued)

(58) Field of Classification Search
CPC .............. A61B 1/0057; A61B 1/0052; A61M 25/0136; A61M 25/0147; A61M 2025/015
(Continued)

(56) References Cited

U.S. PATENT DOCUMENTS

| RE34,502 E | 1/1994 | Webster, Jr. |
| 5,364,352 A | 11/1994 | Cimino et al. |

(Continued)

FOREIGN PATENT DOCUMENTS

| CN | 1093933 A | 10/1994 |
| CN | 101415362 A | 4/2009 |

(Continued)

OTHER PUBLICATIONS

Partial European Search Report mailed on Apr. 3, 2013 from corresponding European Patent Application No. 12199721.7.

(Continued)

*Primary Examiner* — Theodore Stigell
*Assistant Examiner* — Benjamin Koo
(74) *Attorney, Agent, or Firm* — Roberts Mlotkowski Safran Cole & Calderon, P.C.

(57) ABSTRACT

A medical device control handle or catheter includes deflection assembly and at least one of the following: a disk actuator, a lever actuator and a ring actuator for actuating additional puller wires in manipulation of multiple features of the medical device or catheter independently of each other. The disk actuator has a common rotational axis with but is rotationally independent of the deflection assembly. The lever actuator has a separate rotational axis. The ring is mounted outside of the control handle and rotatable relative to the control handle to actuate another puller wire for manipulating another feature of the catheter.

Each of the disk, lever and ring actuators are of a design that allows existing control handles and catheters to be readily modified to include these actuators.

9 Claims, 18 Drawing Sheets

(51) Int. Cl.
*A61B 5/042* (2006.01)
*A61B 5/00* (2006.01)
*A61B 1/005* (2006.01)
*A61B 5/06* (2006.01)
*A61B 18/00* (2006.01)

(52) U.S. Cl.
CPC ..... *A61B 18/1492* (2013.01); *A61M 25/0147* (2013.01); *A61B 1/0052* (2013.01); *A61B 1/0057* (2013.01); *A61B 5/065* (2013.01); *A61B 5/6852* (2013.01); *A61B 2018/0091* (2013.01); *A61B 2018/1435* (2013.01)

(58) Field of Classification Search
USPC ............ 604/95.01, 95.04, 528; 606/106–115
See application file for complete search history.

(56) References Cited

U.S. PATENT DOCUMENTS

| | | | |
|---|---|---|---|
| 5,441,483 A | 8/1995 | Avitall | |
| 5,702,433 A | 12/1997 | Taylor et al. | |
| 6,530,913 B1 | 3/2003 | Giba et al. | |
| 6,554,794 B1 | 4/2003 | Mueller et al. | |
| 6,610,058 B2 | 8/2003 | Flores | |
| 7,011,655 B2 | 3/2006 | Thompson et al. | |
| 7,025,759 B2 | 4/2006 | Muller | |
| 7,269,453 B2 | 9/2007 | Mogul | |
| 7,374,553 B2 | 5/2008 | Koerner et al. | |
| 7,377,906 B2 | 5/2008 | Selkee | |
| 7,682,358 B2 | 3/2010 | Gullickson et al. | |
| 7,803,130 B2 | 9/2010 | Ryan et al. | |
| 7,815,637 B2 | 10/2010 | Ormsby et al. | |
| 2004/0116849 A1 | 6/2004 | Gardeski | |
| 2005/0256452 A1 | 11/2005 | DeMarchi et al. | |
| 2006/0252993 A1 | 11/2006 | Freed et al. | |
| 2009/0281524 A1 | 11/2009 | Scheibe et al. | |
| 2010/0004591 A1 | 1/2010 | Barenboym et al. | |
| 2010/0004633 A1 | 1/2010 | Rothe et al. | |
| 2011/0054287 A1 | 3/2011 | Schultz | |

FOREIGN PATENT DOCUMENTS

| | | |
|---|---|---|
| CN | 102000379 A | 4/2011 |
| EP | 2 289 592 A2 | 3/2011 |
| WO | WO 2005/094665 A2 | 10/2005 |

OTHER PUBLICATIONS

Extended European Search Report mailed on Jul. 25, 2013 from corresponding European Patent Application No. 12199721.7.
SIPO Office action dated Dec. 28, 2015, with English translation, for Chinese Patent application 201210579799.5, (11 pages).
SIPO Search Report dated Dec. 17, 2015 issued in CN Application No. 201210579799.5, 2 pages.

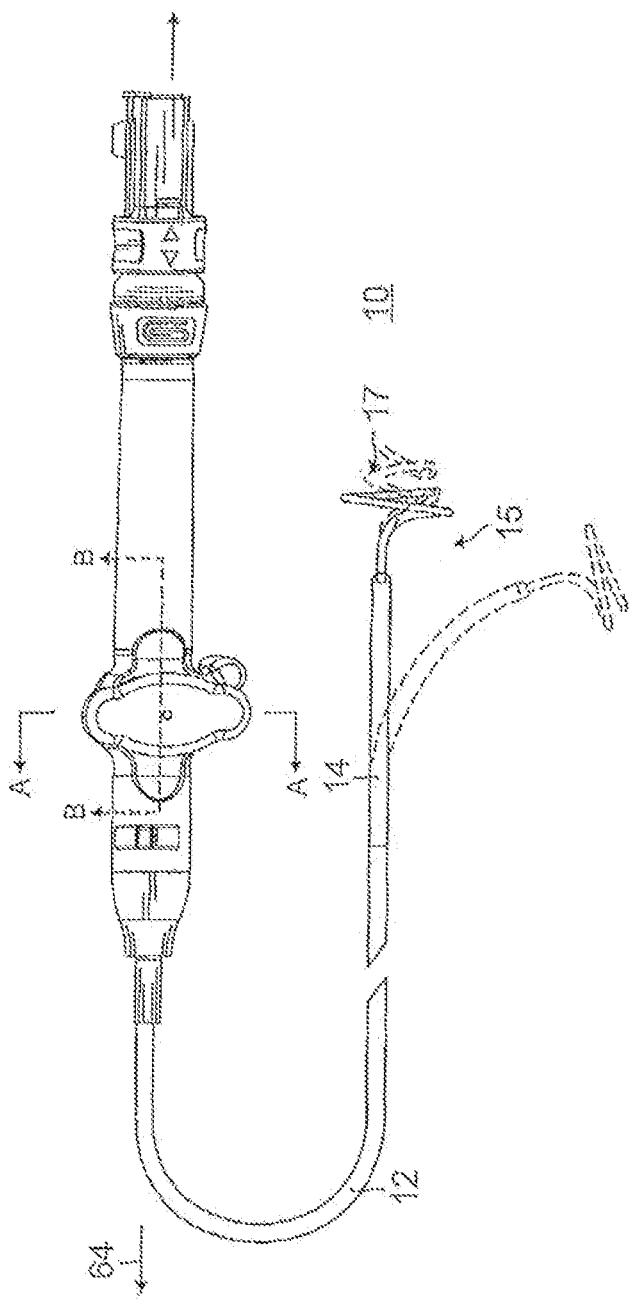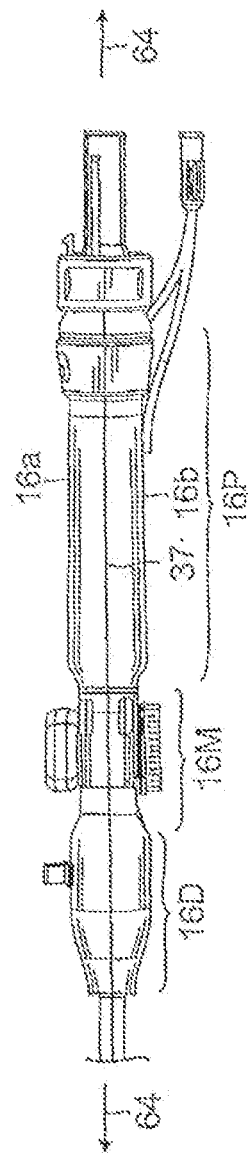
FIG. 1
FIG. 1C

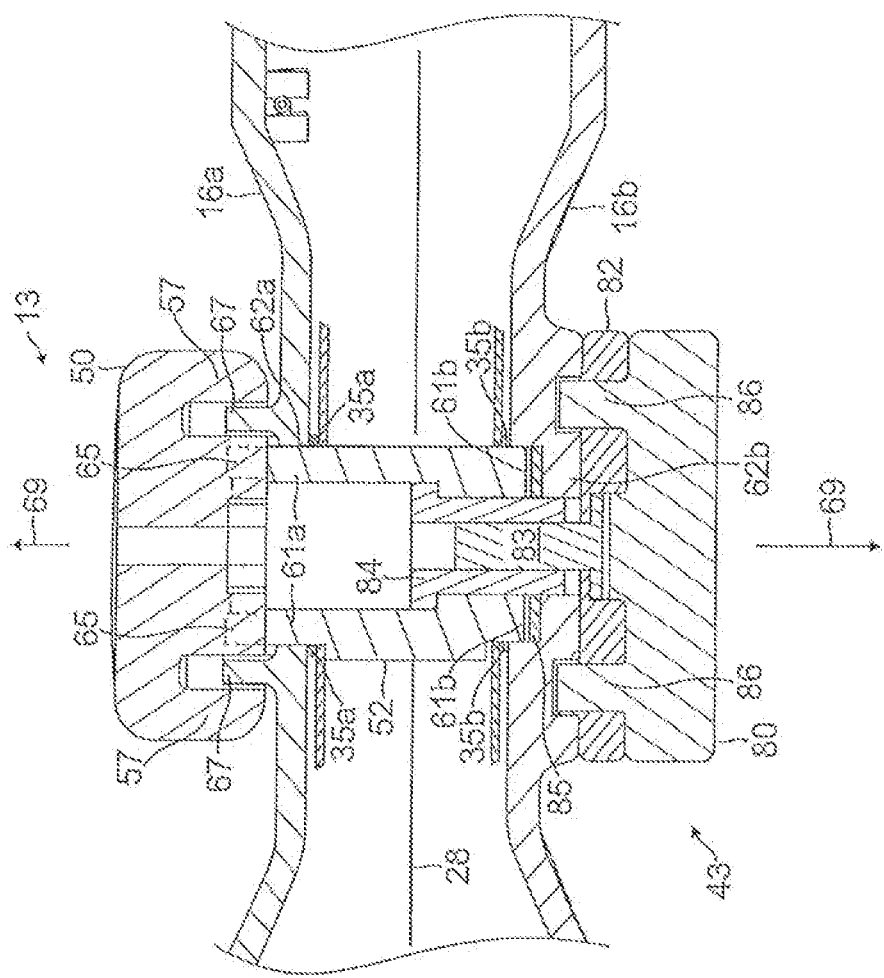

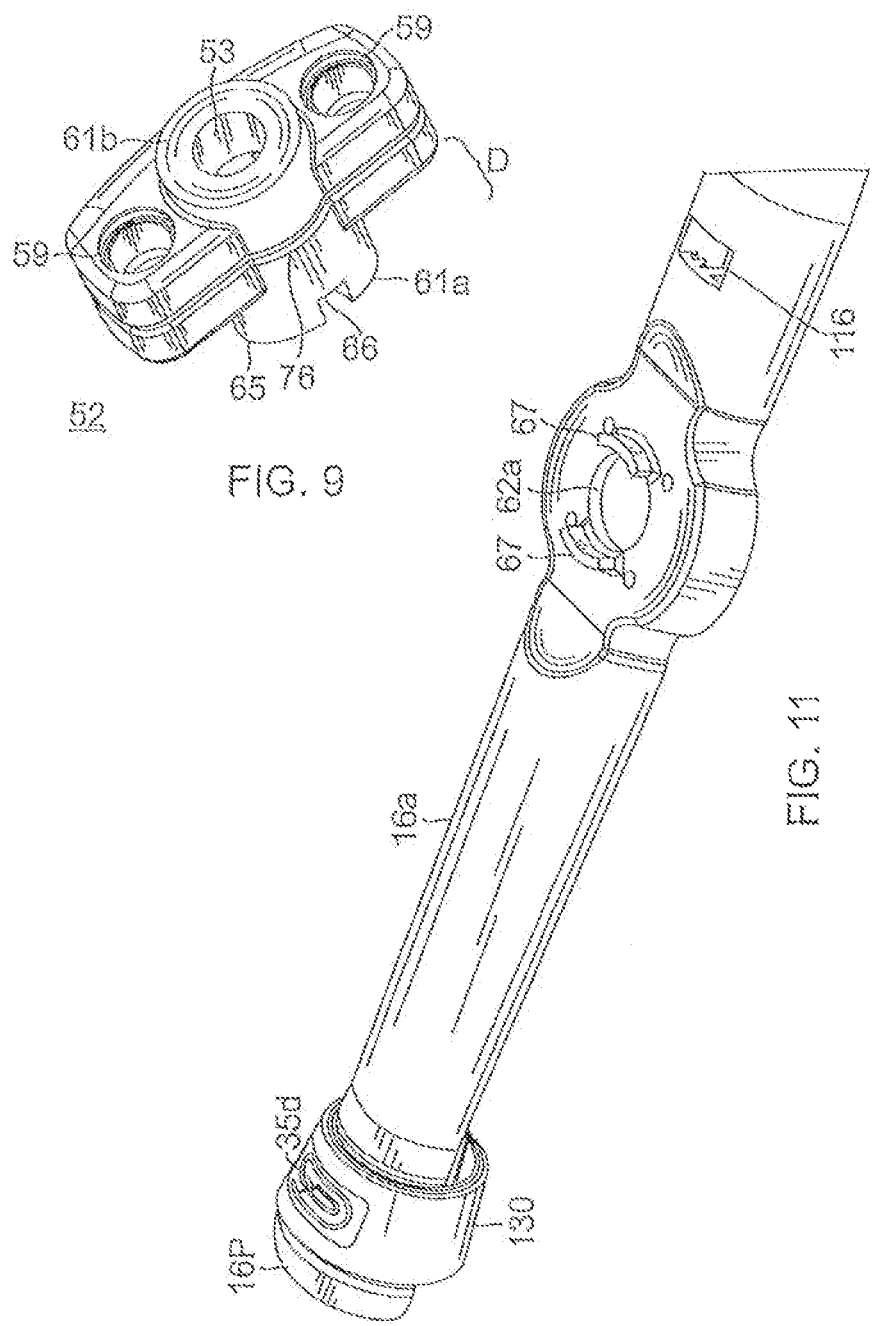

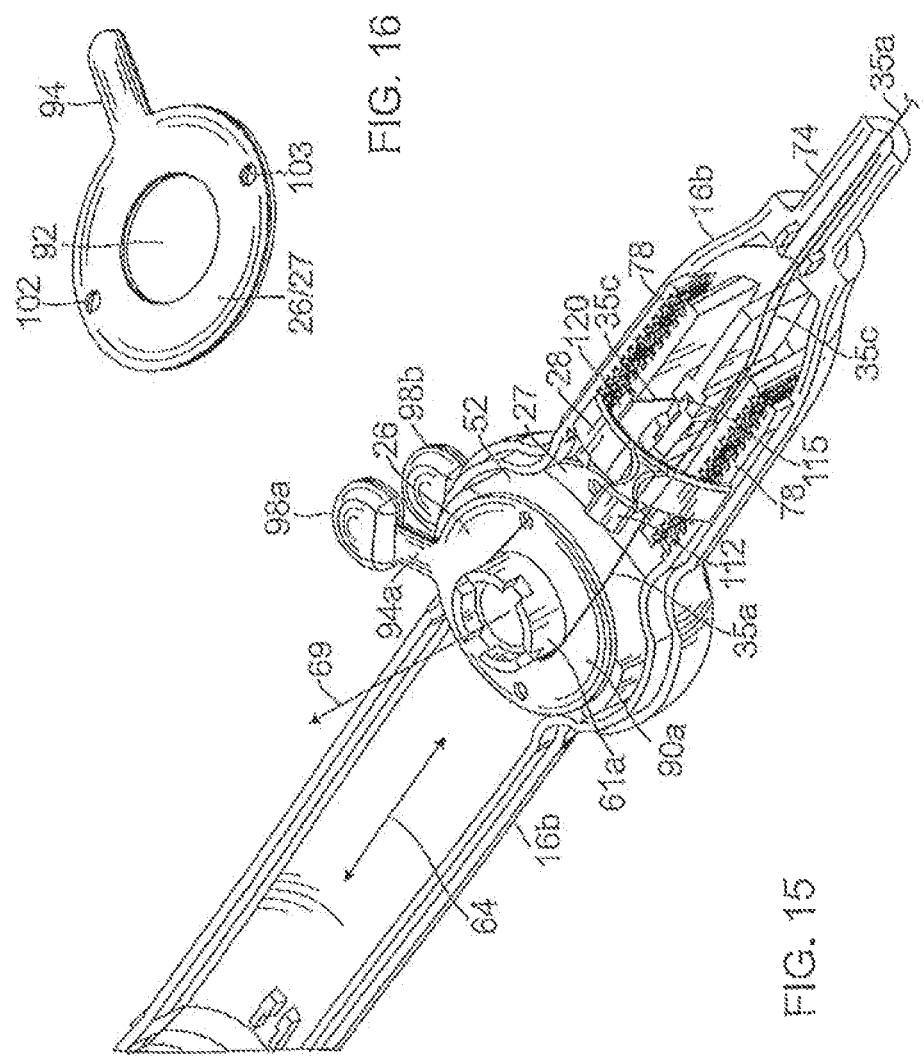

MEDICAL DEVICE CONTROL HANDLE WITH MULTIPLE PULLER WIRES

RELATED APPLICATION

This application is a divisional application of U.S. Ser. No. 13/341,840 filed on Dec. 30 2011, now issued U.S. Pat. No. 9,162,036, the complete disclosure of which is hereby incorporated herein by reference for all purposes.

FIELD OF INVENTION

This invention relates to a control handle for medical devices, in particular, a control handle having mechanisms controlling multiple puller wires.

BACKGROUND

Electrode catheters have been in common use in medical practice for many years. They are used to stimulate and map electrical activity in the heart and to ablate sites of aberrant electrical activity. Atrial fibrillation is a common sustained cardiac arrhythmia and a major cause of stroke. This condition is perpetuated by reentrant wavelets propagating in an abnormal atrial-tissue substrate. Various approaches have been developed to interrupt wavelets, including surgical or catheter-mediated atriotomy. Prior to treating the condition, one has to first determine the location of the wavelets. Various techniques have been proposed for making such a determination, including the use of catheters with a mapping assembly that is adapted to measure activity within a pulmonary vein, coronary sinus or other tubular structure about the inner circumference of the structure. One such mapping assembly has a tubular structure comprising a generally circular main region generally transverse and distal to the catheter body and having an outer circumference and a generally straight distal region distal to the main region. The tubular structure comprises a non-conductive cover over at least the main region of the mapping assembly. A support member having shape-memory is disposed within at least the main region of the mapping assembly. A plurality of electrode pairs, each comprising two ring electrodes, are carried by the generally circular main region of the mapping assembly.

In use, the electrode catheter is inserted into a guiding sheath which has been positioned a major vein or artery, e.g., femoral artery, and guided into a chamber of the heart. Within the chamber, the catheter is extended past a distal end of the guiding sheath to expose the mapping assembly. The catheter is maneuvered through movements that include deflection of a distal portion of the catheter so that the mapping assembly is positioned at the tubular region in the heart chamber. The ability to control the exact position and orientation of the catheter and also the configuration of the mapping assembly is critical and largely determines how useful the catheter is.

Steerable catheters are generally well-known. For example, U.S. Pat. No. Re 34,502 describes a catheter having a control handle comprising a housing having a piston chamber at its distal end. A piston is mounted in the piston chamber and is afforded lengthwise movement. The proximal end of the elongated catheter body is attached to the piston. A puller wire is attached to the housing and extends through the piston, through the catheter body, and into a tip section at the distal end of the catheter body. The distal end of the puller wire is anchored in the tip section of the catheter. In this arrangement, lengthwise movement of the piston relative to the housing results in deflection of the catheter tip section.

The design described in U.S. Pat. No. RE 34,502 is generally limited to a catheter having a single puller wire. If bi-directional deflection is desire, more than one puller wire becomes necessary. Moreover, if more control is desired, such as contraction of the mapping assembly, an additional puller wire is needed. Accordingly, a need exists for a control handle capable of controlling multiple puller wires with mechanisms which occupy minimal space within a control handle and which design is adaptable to existing control handles.

SUMMARY OF THE INVENTION

The present invention is directed to a medical device control handle or catheters. As medical devices, especially, electrophysiological catheters, become more complex with more components to actuate, a control handle should provide independent control of multiple puller members. The control handle of the present invention includes a disk actuator, a lever actuator and a ring actuator for actuating three different puller wires in manipulation of multiple features of the medical device independently of each other.

In one embodiment, the control handle has a housing, a deflection assembly having a deflection knob and a pulley arm to which deflection puller wire(s) are coupled to for deflecting a portion of the medical device in response to rotation of the deflection knob by a user. The control handle also has a disk actuator that has a common rotational axis with the deflection assembly as the disk actuator is mounted on a portion of the pulley arm but is rotationally independent of the pulley arm. The disk actuator has a tab that extends through an opening formed in the control handle housing so that it is accessible to the user outside of the housing. The tab is in close proximity to the deflection knob so that the user can easily control both, even with one hand.

In another embodiment, the control handle has a lever actuator in addition to the deflection assembly, where the lever actuator has a separate rotational axis from that of the pulley arm. The lever actuator controls an additional puller wire for manipulating another feature of the catheter. In a more detailed embodiment, the lever actuator is distal of the pulley arm and its rotational axis is oriented generally perpendicular of the rotational axis of the pulley arm. The control handle housing has an opening through which a tab of the lever actuator extends so that it is accessible to the user outside of the housing.

In yet another embodiment, the control handle has a ring actuator in addition to the deflection assembly. The ring is mounted outside of the control handle and rotatable relative to the control handle to actuate another puller wire for manipulating another feature of the catheter. Each of the disk, lever and ring actuators are of a design that allows existing control handles and catheters to be readily modified to include these actuators. The disk actuator can be mounted on existing pulley arms with minor modifications to existing control handles. The lever actuator and ring actuator can be mounted on existing control handles with minor modifications.

BRIEF DESCRIPTION OF THE DRAWINGS

These and other features and advantages of the present invention will be better understood by reference to the following detailed description when considered in conjunction with the accompanying drawings. It is understood that selected structures and features have not been shown in certain drawings so as to provide better viewing of the remaining structures and features.

FIG. 1 is a side elevational plan view of one embodiment of the catheter of the present invention.

FIG. 1B is a side cross-sectional view of the control handle of FIG. 1, taken along line B-B.

FIG. 1C is a top plan view of the catheter of FIG. 1.

FIG. 9 is a perspective view of the pulley arm of FIG. 8B

FIG. 11 is a perspective view of an outer surface of an embodiment of a first control handle housing half.

FIG. 15 is a perspective view of the inner surface of an embodiment of the second control handle housing half, with the first and second disk actuators and a lever actuator.

FIG. 16 is a perspective view of the disk actuator of FIG. 15.

DETAILED DESCRIPTION OF THE INVENTION

Figure 1A:
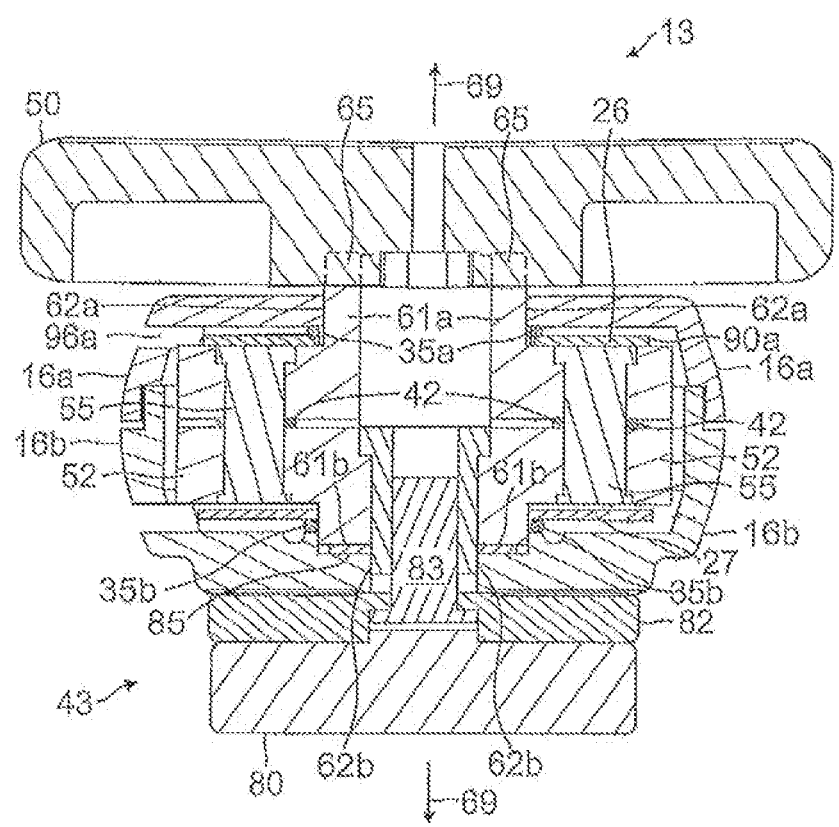
FIG. 1A is an end cross-sectional view of a control handle of FIG. 1, taken along line A-A.

The present invention is directed to a control handle 16 for use with a medical device with at least two tensile puller members, e.g., puller wires or the like, for actuating at least two independent movements or manipulations of components of the medical device. The control handle may be used with any variety of medical devices, for example, an electrophysiological (EP) catheter 10 configured for mapping and/or ablation of tissue, including the heart, an embodiment of which is illustrated in FIG. 1.

The catheter 10 of FIG. 1 comprises an elongated catheter body 12, a deflectable intermediate section 14 at a distal end of the catheter body 12, and a tip section 15 including a distal assembly 17 having, for example, a helical form, at a distal end of the intermediate section 14. The catheter includes a control handle 16 with multiple puller wire actuators, including actuators for uni- or bi-directional deflection of the intermediate section and manipulation of the distal assembly, for example, to contract the helical form of the distal assembly. Each actuator can be operated separately and independently without affecting the other actuator or its puller wire(s).

Figure 2A:
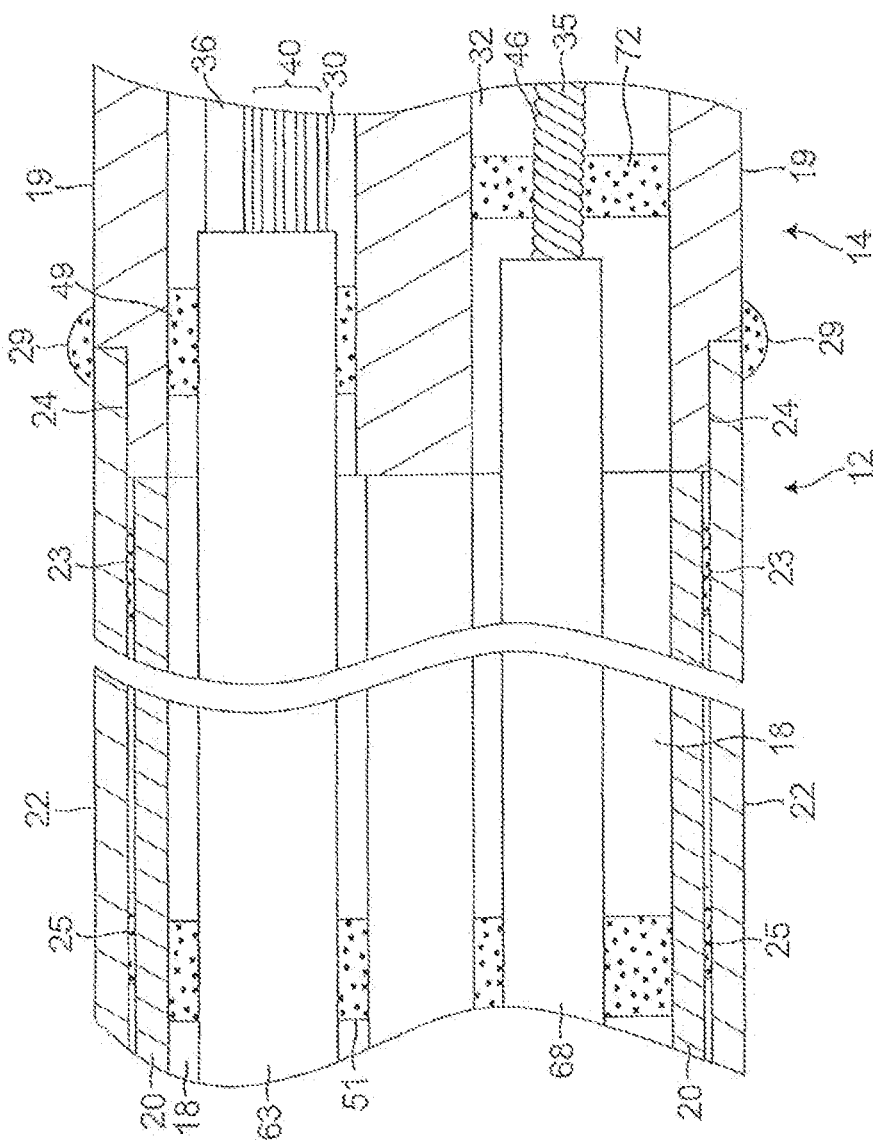
FIG. 2A is a side cross-sectional view of an embodiment of a junction of a catheter body and an intermediate section, taken along a first diameter.
Figure 2B:
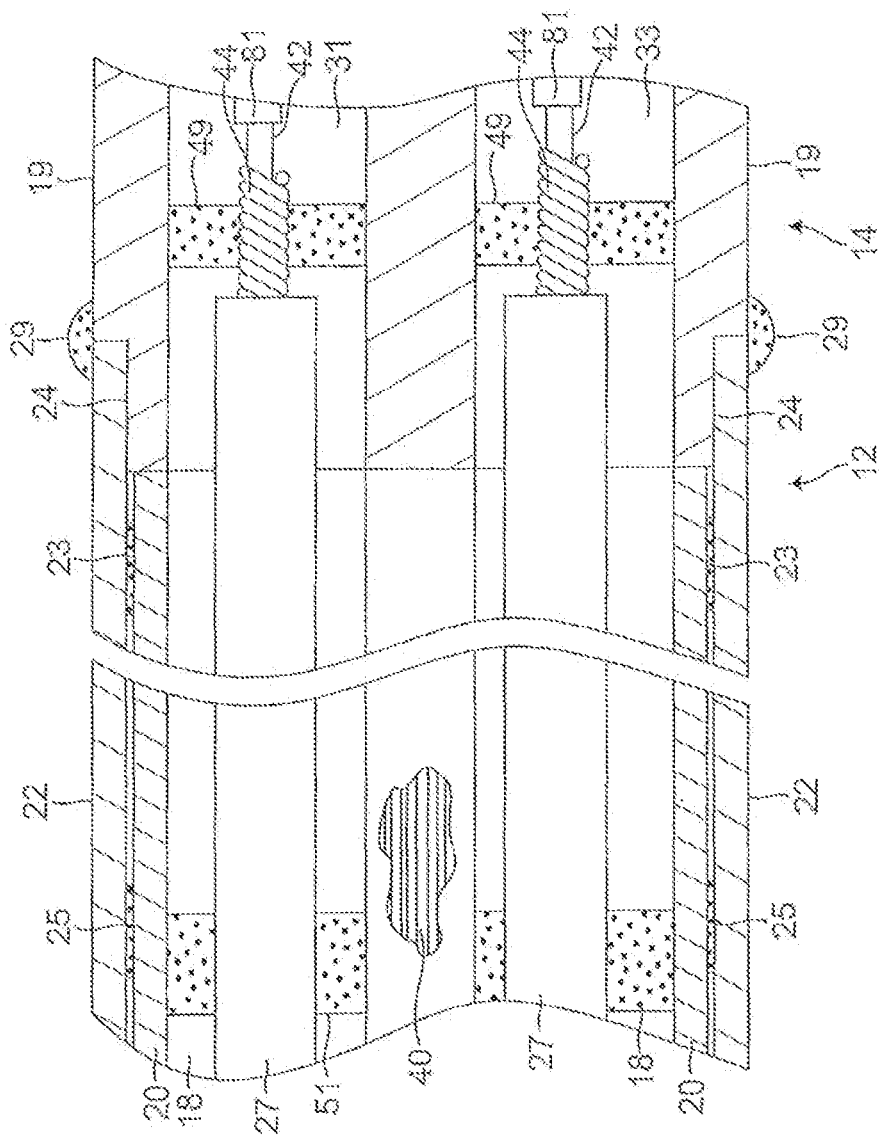
FIG. 2B is a side cross-sectional view of the embodiment of the junction of FIG. 2A, taken along a second diameter generally perpendicular to the first diameter.

With reference to FIGS. 2A and 2B, the catheter body 12 comprises a single, central or axial lumen 18. The catheter body 12 is flexible, i.e., bendable, but substantially non-compressible along its length. The catheter body 12 may be of any suitable construction and made of any suitable material. In one embodiment, the catheter body 12 comprises an outer wall 22 made of a polyurethane or PEBAX. The outer wall 22 comprises an imbedded braided mesh of stainless steel or the like to increase torsional stiffness of the catheter body 12 so that, when the control handle 16 is rotated, the tip section of the catheter 10 will rotate in a corresponding manner.

The outer diameter of the catheter body 12 is not critical, but is preferably no more than about 8 French. Likewise the thickness of the outer wall 22 is not critical. The inner surface of the outer wall 22 is lined with a stiffening tube 20, which can be made of any suitable material, preferably polyimide. The stiffening tube 20 is held in place relative to the outer wall 22 at the proximal end of the catheter body 12. A first glue joint 23 is made between the distal ends of the stiffening tube 20 and the outer wall 22 by a fast drying glue, e.g. Super Glue™. Thereafter, a second glue joint 25 is formed between the proximal ends of the stiffening tube 20 and outer wall 22 using a slower drying but stronger glue, e.g., polyurethane.

The stiffening tube 20, along with the braided outer wall 22, provides improved torsional stability while at the same time minimizing the wall thickness of the catheter, thus maximizing the diameter of the single lumen. The outer diameter of the stiffening tube 20 is about the same as or slightly smaller than the inner diameter of the outer wall 22. Polyimide tubing is suitable because it may be very thin walled while still providing very good stiffness. This maximizes the diameter of the central lumen 18 without sacrificing strength and stiffness. Polyimide material is typically not used for stiffening tubes because of its tendency to kink when bent. However, it has been found that, in combination with an outer wall 22 of polyurethane, PEBAX or other similar material, particularly having a stainless steel braided mesh, the tendency for the polyimide stiffening tube 20 to kink when bent is essentially eliminated with respect to the applications for which the catheter is used. In one embodiment, the outer wall 22 has an outer diameter of about 0.092 inch and an inner diameter of about 0.063 inch and the polyimide stiffening tube 20 has an outer diameter of about 0.0615 inch and an inner diameter of about 0.052 inch.

Figure 3:
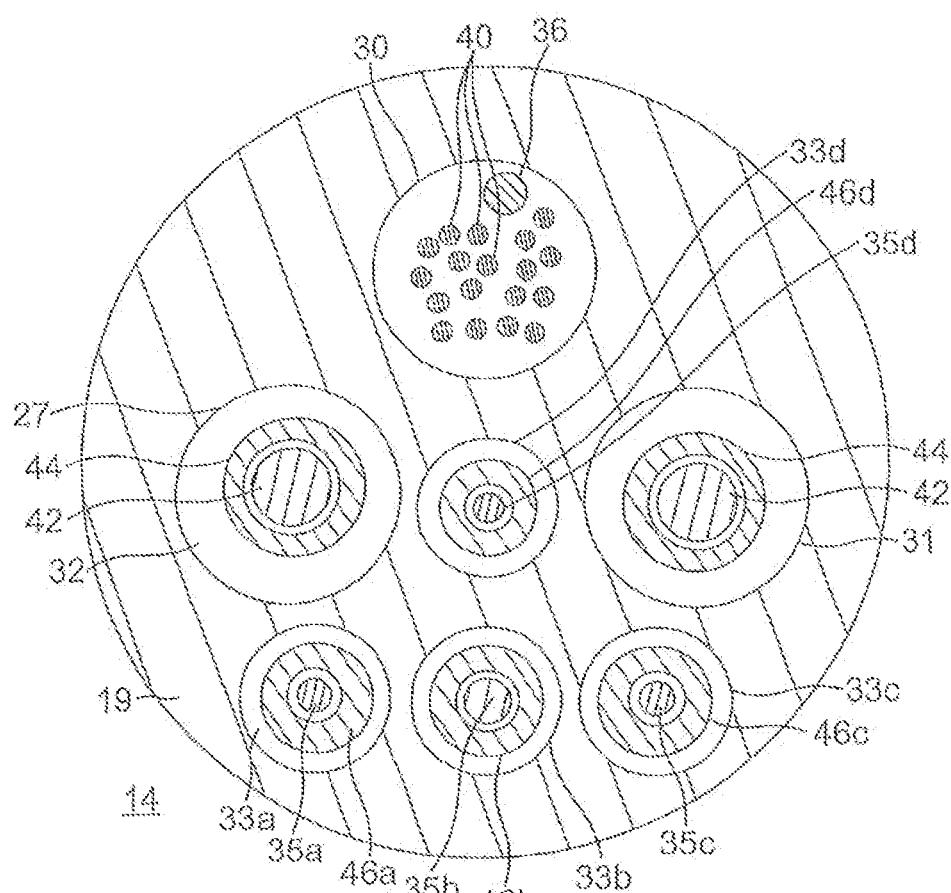
FIG. 3 is an end cross-sectional view of the intermediate section of FIGS. 2A and 2B.

As shown in FIGS. 2A, 2B and 3, the intermediate section 14 comprises a shorter section of tubing 19 with multiple lumens, for example, first, second and third lumens 30, 31, and 32. In the disclosed embodiment, the tubing 19 also includes fourth, fifth, sixth and seven lumens 33a, 33b, 33c and 33d. The tubing 19 is made of a suitable non-toxic material which is preferably more flexible than the catheter body 12. A suitable material for the tubing 19 is braided polyurethane, i.e., polyurethane with an embedded mesh of braided stainless steel or the like. The outer diameter of the intermediate section 14, like that of the catheter body 12, is preferably no greater than about 8 French. The size of the lumens is not critical. In one embodiment, the intermediate section has an outer diameter of about 7 French (0.092 inch) and the lumens are generally about the same size, having a diameter of about 0.022 inch, or selected lumens can have a slightly larger diameter of about 0.036 inch.

A means for attaching the catheter body 12 to the intermediate section 14 is illustrated in FIGS. 2A and 2B. The proximal end of the intermediate section 14 comprises an inner counter bore 24 that receives the wall 22. The intermediate section 14 and catheter body 12 are attached by glue 29 or the like.

As shown in FIGS. 2A and 2B, extending through the single lumen 18 of the catheter body 12 are various components, for example, lead wires and multiple puller wires, and any other wires or cables. Longitudinal movement of the puller wires relative to the catheter body 12 enables user control of various parts of the catheter via the control handle. As mentioned, in one embodiment, there are at least first and second deflection puller wires 42 for deflecting the intermediate section 14 and a third puller wire 35a for manipulating and adjusting the distal assembly 17 of the tip section 15. The catheter may include additional puller wires, for example, fourth, fifth and sixth puller wires 35b, 35c and 35d for manipulating and adjusting additional features of the distal assembly. Each puller wire 42 is made of any suitable metal, such as stainless steel or Nitinol. Preferably each puller wire has a low friction coating, such as a coating of Teflon™ or the like. Each puller wire has a diameter preferably ranging from about 0.006 inch to about 0.012 inch. Preferably both of the puller wires have the same diameter. Flat puller wires may be used in place of round puller wires. Their cross sectional dimensions should be such that they provide comparable tensile strengths as round puller wires.

Alternatively, the puller wires may be replaced in its entirety or in part by tensile fibers. The fibers may be of a high modulus fiber material, preferably having an ultimate tensile strength substantially in the range of 412-463 ksi (2480-3200 Mpa) such as High Molecular Density Polyethylene (e.g., Spectra™ or Dyneema™), a spun para-aramid fiber polymer (e.g., Kevlar™) or a melt spun liquid crystal polymer fiber rope (e.g., Vectran™), or a high strength ceramic fiber (e.g., Nextel™). The term fiber is used herein interchangeably with the term fibers in that the tensile fiber may be of a woven or braided construction. In any case, these materials tend to be flexible, providing suitable durability when used in wrapped engagement with the pulleys and the like for greater throw in deflecting the catheter tip. Further, they are substantially non-stretching, which increases the responsiveness to the manipulation of the control handle, and nonmagnetic so that they generally appear transparent to an MRI. The low density of the material causes it to be generally transparent to an x-ray machine. The materials can also be nonconductive to avoid shorting. Vectran™, for example, has high strength, high abrasion resistance, is an electrical insulator, nonmagnetic, is polymeric, and has low elongation under sustained loading conditions. It is therefore understood that the term "wire" as used herein may be a wire, a tensile fiber, or a tensile member comprising wire segment(s) and tensile fiber segment(s).

A single lumen catheter body 12 may be preferred over a multi-lumen body because the single lumen 18 body can permit better tip control when rotating the catheter 10. The single lumen 18 permits the components passing therethrough to float freely within the catheter body. If such components were restricted within multiple lumens, they can build up energy when the handle 16 is rotated, resulting in the catheter body 12 having a tendency to rotate back if, for example, the handle is released, or if bent around a curve, to flip over, either for which are undesirable performance characteristics.

As also shown in FIG. 3, one deflection puller wire 42 extends through the central lumen 18 of the catheter body 12 and into the second lumen 31 of the intermediate section 14. Another deflection puller wire 42 extends through the central lumen 18 and into the third lumen 32 of the intermediate section 14. In that regard, the lumens 31, 32 should be off-axis and diametrically opposed to each other for bi-directional deflection in a plane. The distal ends of the deflection puller wires 42 are anchored to the wall of the tubing 19 near the distal end of the intermediate section 14 by means of T-anchors (not shown) as understood by one of ordinary skill in the art. In the intermediate section 14, each deflection puller wires 42 extends through a plastic, e.g. Teflon™, sheath 81, which prevents the deflection puller wires 42 from cutting into the wall of the tubing 19 of the intermediate section 14 when the intermediate section 14 is deflected.

As shown in FIG. 2B, compression coils 44 in surrounding relation to the deflection puller wires 42 extend from the proximal end of the catheter body 12 to the proximal end of the intermediate section 14. The compression coils 44 are made of any suitable metal, e.g., stainless steel. The compression coils 44 are tightly wound on itself to provide flexibility, i.e., bending, but to resist compression. The inner diameter of the compression coils 44 is preferably slightly larger than the diameter of the puller wires 42. For example, when a puller wire 42 has a diameter of about 0.007 inches, the compression coil 44 preferably has an inner diameter of about 0.008 inches. The Teflon™ coating on the puller wire 42 allows them to slide freely within the compression coils 44. The outer surface of the compression coils 44 is covered by a flexible, non-conductive sheath 27 to prevent contact between the compression coils 44 and other components, such as lead wires and cables, etc. In one embodiment, a non-conductive sheath is made of polyimide tubing.

The compression coils 44 are anchored at their proximal ends to the proximal end of the stiffening tube 20 in the catheter body 12 by glue joint 51 (FIG. 2B) and at its distal end near the proximal end of the intermediate section 14 in the second lumen 31 and third lumen 32 by glue joints 49 (FIG. 2B).

Figure 4:
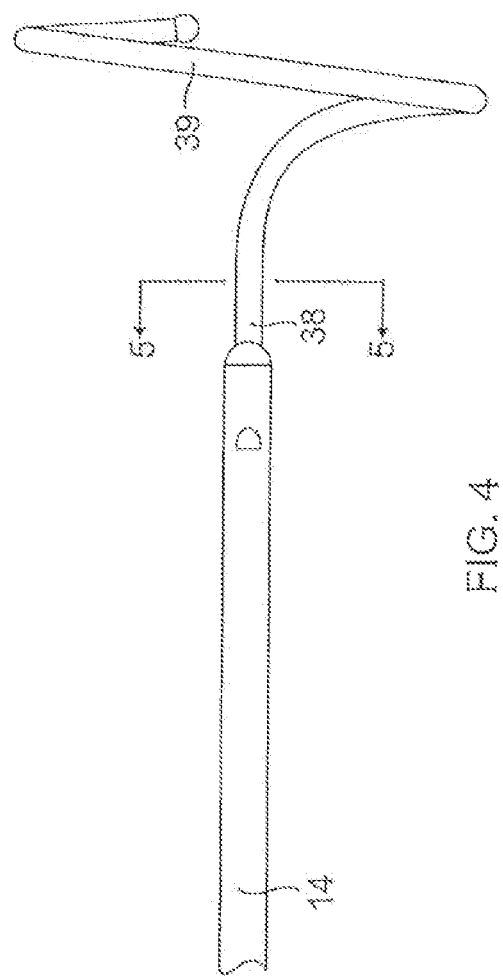
FIG. 4 is a side elevational view of an embodiment of a distal assembly.
Figure 5:
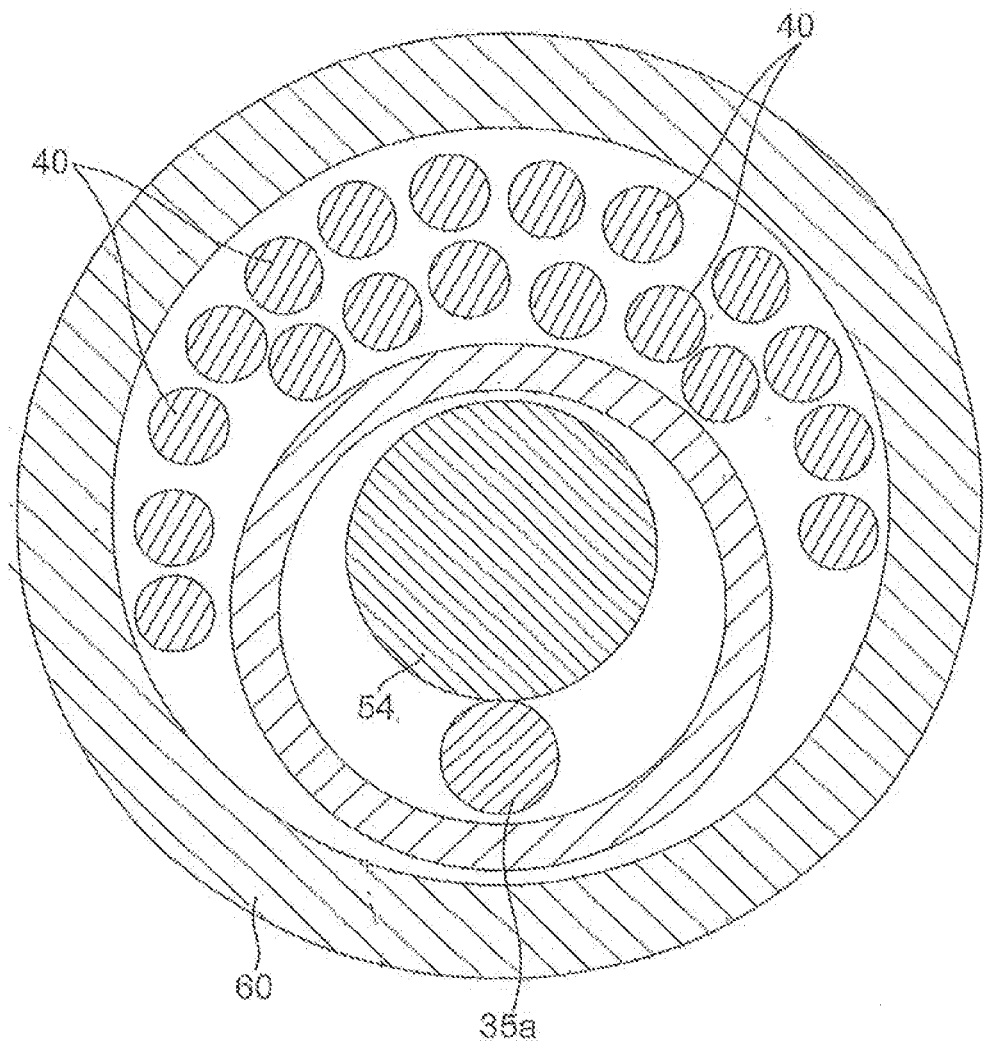
FIG. 5 is an end cross-sectional view of a generally straight proximal portion of the distal assembly of FIG. 4, taken along line 5-5.

With reference to FIG. 4, at the distal end of the intermediate section 14 is the distal assembly 17. The distal assembly 17 comprises a generally straight proximal region 38 and a generally circular main region 39. The proximal region 38 is mounted on the intermediate section 14 and the main region 39 carries a plurality of electrodes for mapping and/or ablation. In the embodiment of FIG. 5, the distal assembly 17 includes a tubing 60. A shape memory member 54 and lead wires 40 for electrodes carried on the distal assembly extend through the lumen of the tubing 60 and into the intermediate section 14 and the catheter body 12.

In the disclosed embodiment, the third or contraction puller wire 35a is provided to contract the generally circular main region 39 to thereby change or reduce its diameter, for example, when mapping or ablating circular or tubular regions of the heart. The contraction wire 35a has a proximal end anchored in the control handle 16 as described further below. The contraction wire 35a extends through the central lumen 18 of the catheter body 12, through the fourth lumen 33a of the intermediate section 14 (FIG. 3) and into the distal assembly 17 (FIG. 5).

A third compression coil 46a is situated within the catheter body 12 and intermediate section shaft 14 in surrounding relation to the contraction wire 35a (FIG. 2A). The third compression coil 46a extends from the proximal end of the catheter body 12 and to near the distal end of the fourth lumen 33a of the intermediate section 14. The third compression coil 46a is made of any suitable metal, such as stainless steel, and is tightly wound on itself to provide flexibility, i.e., bending, but to resist compression. The inner diameter of the third compression coil 46a is preferably slightly larger than the diameter of the contraction wire 35a. The outer surface of the compression coil 46a is covered by a flexible, non-conductive sheath 68a, e.g., made of polyimide tubing. The third compression coil 46a preferably is formed of a wire having a square or rectangular cross-sectional area, which makes it less compressible than a compression coil formed from a wire having a circular cross-sectional area. As a result, the third compression coil 46a keeps the catheter body 12, and particularly the intermediate section 14, from deflecting when the contraction wire 35a is manipulated to contract the distal assembly 17 as it absorbs more of the compression. The compression coil 46a is anchored at its proximal end to the stiffening tube 20 of the catheter body 12 by a proximal glue joint 51 and to the intermediate section 14 by the distal glue joint 49. With reference to the foregoing, it is understood that fourth, fifth and sixth puller wires 35b, 35c and 35d and their respective compression coils 46b, 46c and 46d are similarly structured and situated in the catheter.

Glue joints throughout the catheter 10 may comprise polyurethane glue or the like. The glue may be applied by means of a syringe or the like through a hole made in the tubing walls. Such a hole may be formed, for example, by a needle or the like that punctures the tubing walls where the needle is heated sufficiently to form a permanent hole. The glue is then introduced through the hole to wick around the component(s) within the tubing to form a glue joint about the entire circumference of the component(s).

The lead wires 40 attached to the ring electrodes on the distal assembly 17 extend through the first lumen 30 of the intermediate section 14 (FIG. 2A), through the central lumen 18 of the catheter body 12, through the control handle 16, and terminate at their proximal end in a connector (not shown) which is connected to an appropriate monitor or other device for receiving and displaying the information received from the ring electrodes. The portion of the lead wires 40 extending through the central lumen 18 of the catheter body 12, control handle 16 and proximal end of the intermediate section 14 is enclosed within a protective sheath 63, which can be made of any suitable material, preferably polyimide.

An electromagnetic position sensor (not shown) is mounted in or near the distal assembly 17, e.g., in the distal end of the intermediate section 14. A sensor cable 36 extends from the sensor into the lumen 30 (FIG. 2A) of the intermediate section (along with the electrode lead wires 40), into the central lumen 18 of the catheter body 12 and into the control handle 16 where it terminates in a suitable connector (not shown).

As illustrated in FIG. 1, the control handle 16 comprises a generally elongated handle housing, which can be made of any suitable rigid material. The elongated housing defines a longitudinal axis 64 and can be of a unitary construction or of two opposing halves 16a, 16b that are joined by glue, sonic welding or other suitable means along a seam 37. The housing can be divided into a distal portion 16D, a mid-portion 16M and a proximal portion 16P.

Figure 6:
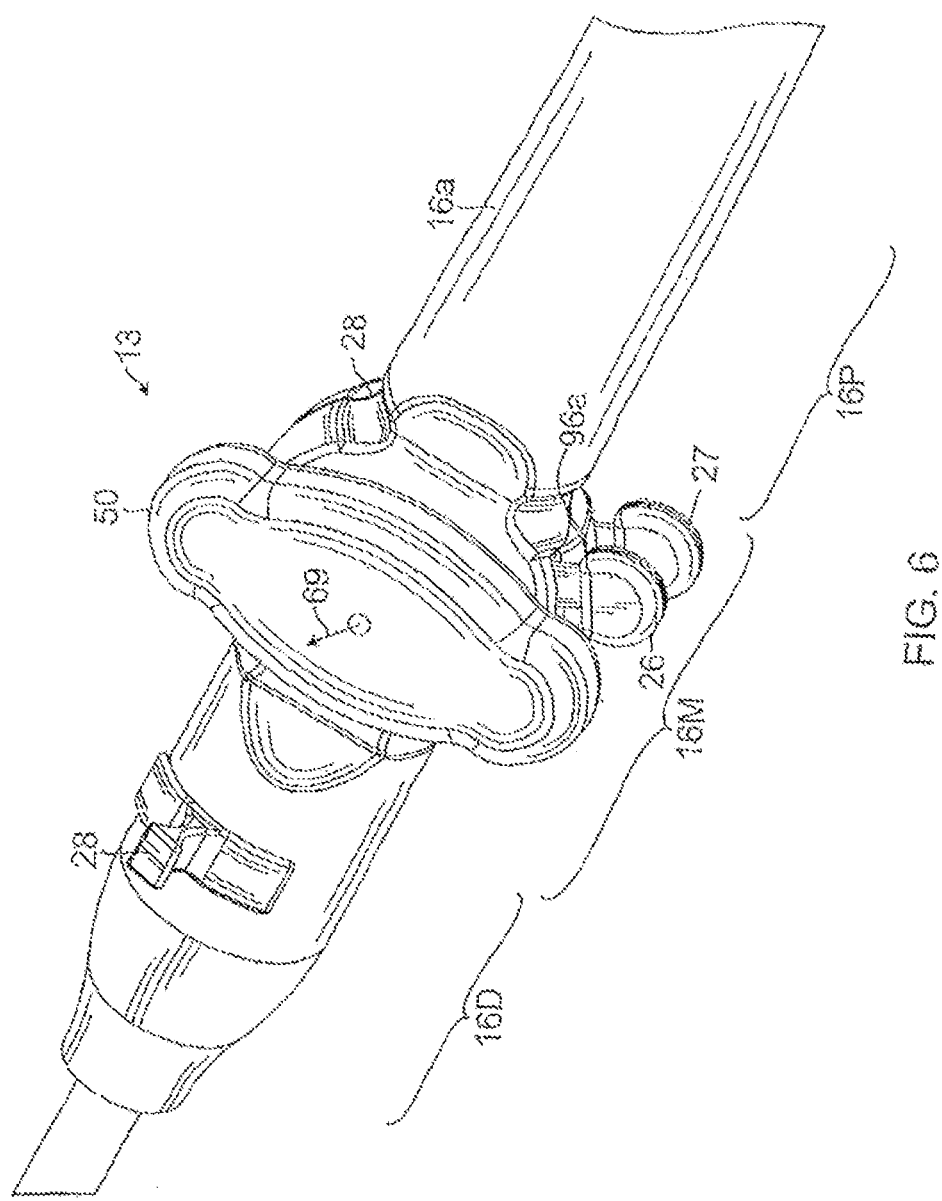
FIG. 6 is a perspective view of a deflection knob, a first disk actuator, a second disk actuator and a lever actuator of the control handle of FIG. 1.

In accordance with the present invention, the control handle 16 provides multiple puller wire actuators. With reference to FIG. 6, the control handle 16 has at the mid-portion 16M a deflection control assembly 13 for bi-directional deflection of the intermediate section 14 by means of the pair of puller wires 42. The mid-portion of the control handle also provides a third puller wire actuator 26 and a fourth puller wire actuator 27.

Figure 7:
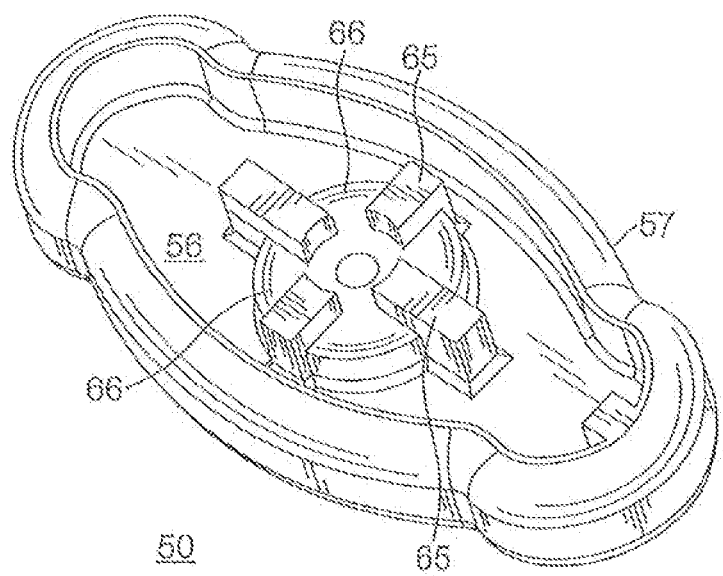
FIG. 7 is a perspective view of an embodiment of a deflection knob of FIG. 6.

With reference to FIGS. 1A and 1B, the deflection control assembly 13 includes a rotatable deflection knob 50 mounted outside of the handle housing 16a and a pulley arm 52 inside the control handle 16 in the mid-portion of the control handle. The knob 50 (FIG. 7) has a generally flat body 56 with a generally oval cross-sectional shape. A peripheral lip 57 surrounds the body 56. Mounted on the control handle 16, the body 56 lies in a plane that is generally parallel with the longitudinal axis 64 of the control handle as best seen in FIG. 1C. The body 56 remains within the plane during rotation of the knob.

Figure 8A:
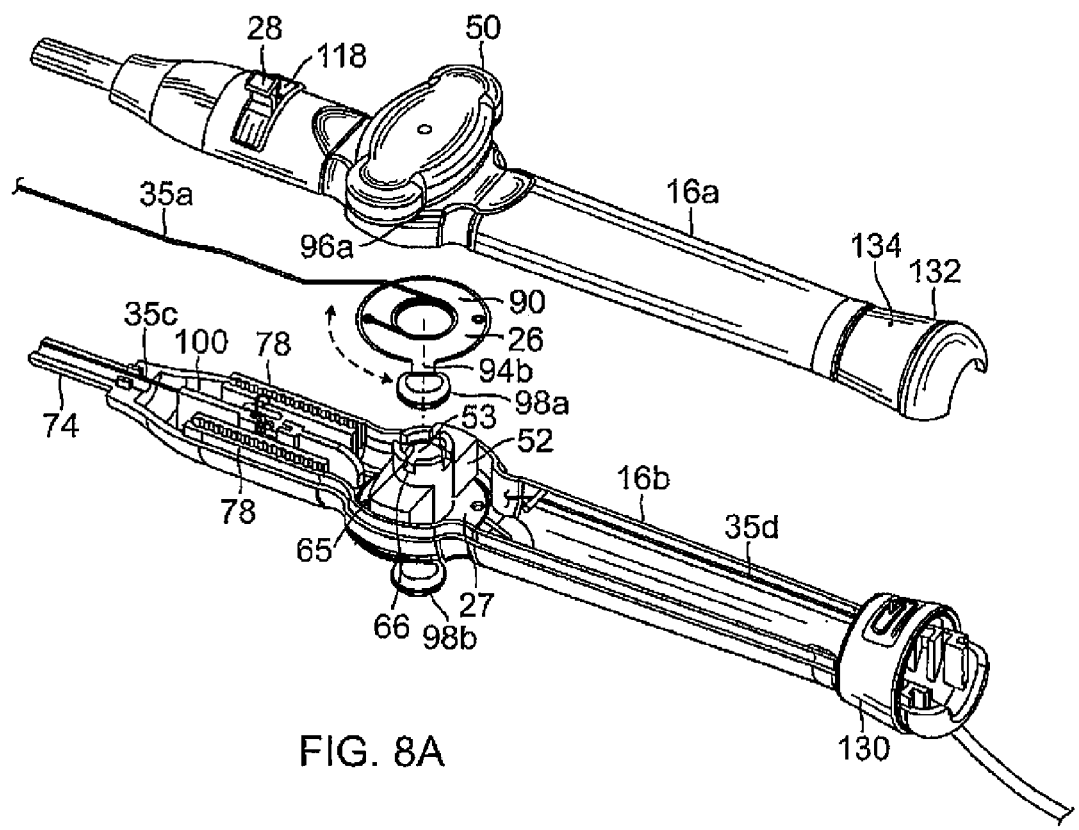
FIG. 8A is an exploded perspective view of an embodiment of the control handle of FIG. 1
Figure 8B:
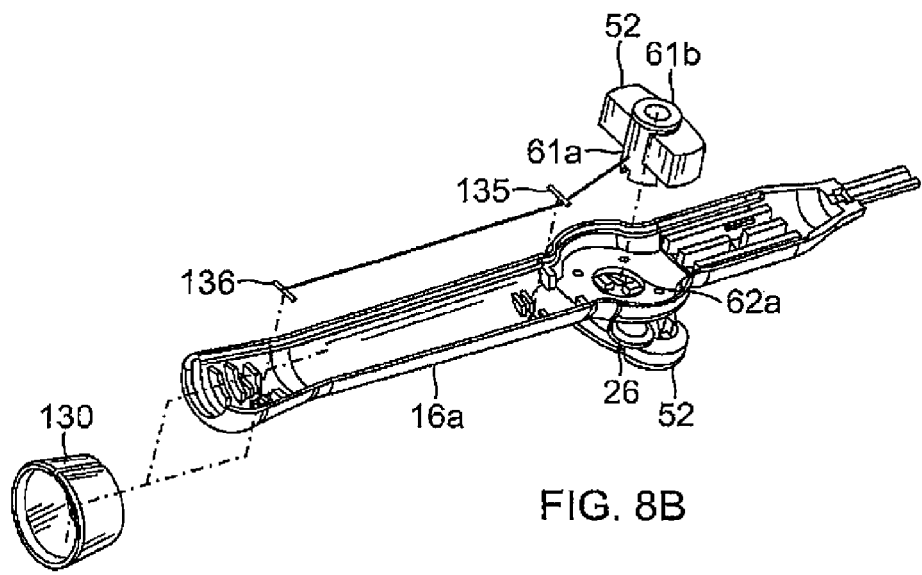
FIG. 8B is an exploded perspective view of selected components of the control handle of FIG. 8A, including a housing half, pulley arm and deflection knob.
Figure 10A:
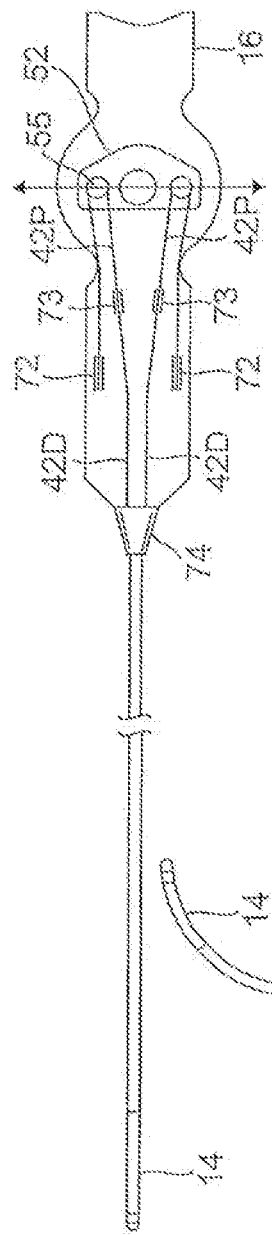
FIG. 10A-10C are schematic diagrams of an embodiment of a control handle of in a neutral configuration, a right deflection configuration, and a left deflection configuration.
Figure 10B:
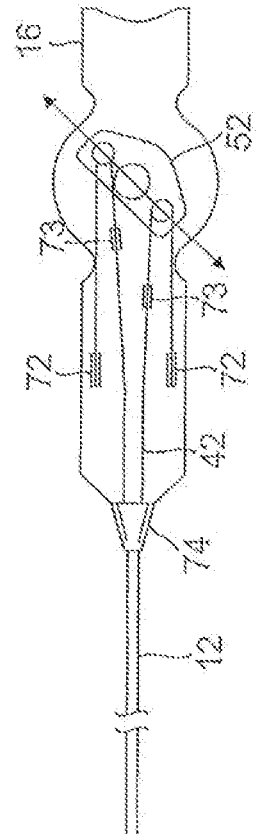
Figure 10C:
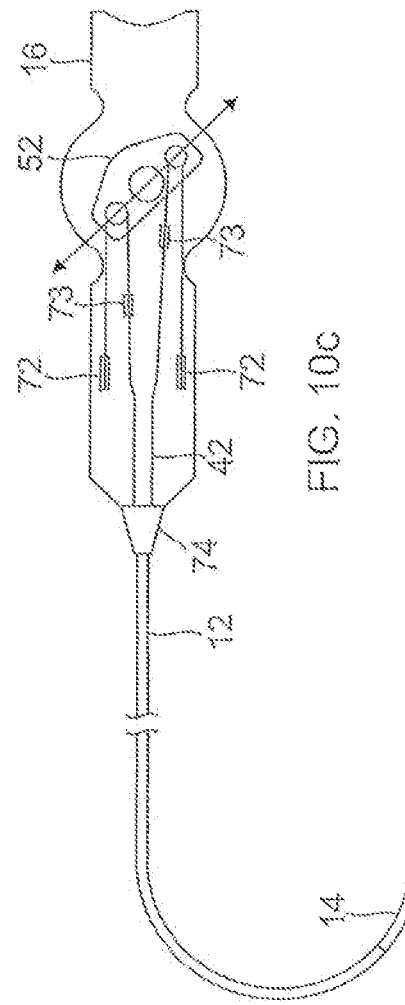

With reference to FIGS. 1A and 9, the pulley arm 52 has a main body with a generally rectangular cross-section and a center bore 53 extending through the main body that divides the body into two halves. In each half is a through-opening 59 that is occupied by a respective pulley 55 (FIG. 1A) adapted to rotate about its own axis. At each end of the center bore 53 is a radial bearing formation 61a and 61b with a circular cross-section. A respective formation is received in a through-hole 62a and 62b formed in the respective control handle housing halves 16a and 16b for supporting the pulley arm 52 within the control handle. The radial bearing formation 61a adjacent the knob has a greater axial dimension D (FIG. 9) than the opposing radial bearing formation 61b for direct rotational coupling with the knob 50 such that the knob 50 and the pulley arm 52 have a common rotational axis 69 that is generally perpendicular to the longitudinal axis 64 of the control handle. In the disclosed embodiment, an interlocking formation of alternating ridges 65 and recesses 66 are provided on interfacing mating surfaces of the knob 50 and the radial bearing formation 61a. Moreover, the ridges 65 (FIG. 7) on an inner mating surface 68 of the knob 50 are elongated to prevent slippage between the knob 50 and the radial bearing formation 61a when the knob is rotated by the user. Moreover, raised guides 67 (FIGS. 1B and 11) are provided on an outer surface of housing handle 16a to block elongated ridges 65 so as to limit the range of rotation of the knob 50 and prevent over-rotation and breakage of deflection puller wires 42. Glue, e.g, epoxy can be applied between the mating surface to adhere the knob 50 and the pulley arm 52, or they can be fastened together with screws or the like. Accordingly, rotation of the knob 50 by the user rotates the pulley arm to actuate the deflection puller wires 42, as illustrated in FIGS. 10A-10C. The pair of bi-directional deflection puller wires 42 enter the control handle 16 via a port 74 in the distal end of the control handle. The puller wires enter the pulley arm 52 through a slit opening 76 (FIG. 9) and each wire is wrapped or wound about a respective pulley 55 (FIG. 1A) about 180 degrees before exiting the pulley arm through the slit opening. A proximal end of each puller member 42 is anchored in a stop 72 that is adjustably but fixedly mounted toothed slots 78 (FIG. 8) in the control handle 16. By rotating the knob 50 in one direction, the pulley arm 52 is rotated in that direction drawing on the puller wire 42 on that side to deflect the intermediate section 14 in that direction. A similar pulley arm is described in U.S. Pat. No. 7,377,906, the entire disclosure of which is hereby incorporated by reference.

Because of the repeated cycles of bending each deflection puller wire 42 can experience around its pulley 55, the segment of each puller wire within the control handle, and especially around the pulleys, may comprise a tensile fiber segment such as described hereinabove, which can better withstand stress and strain. To that end, a crimped connector 73 (FIGS. 10A-10C) is provided to connect a proximal end of each first and second distal puller wire segments 42D to a distal end of a respective proximal tensile fiber segment 42P.

Figure 12:
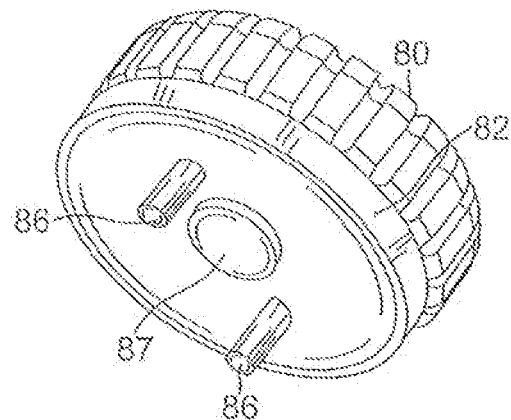
FIG. 12 is a perspective view of an embodiment of a tension adjustment dial and locking plate.
Figure 14:
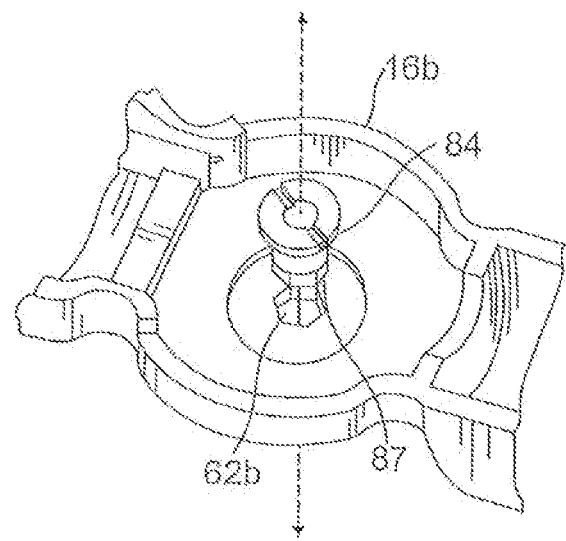
FIG. 14 is a perspective view of an inner surface of an embodiment of the second control handle housing half.
Figure 13:
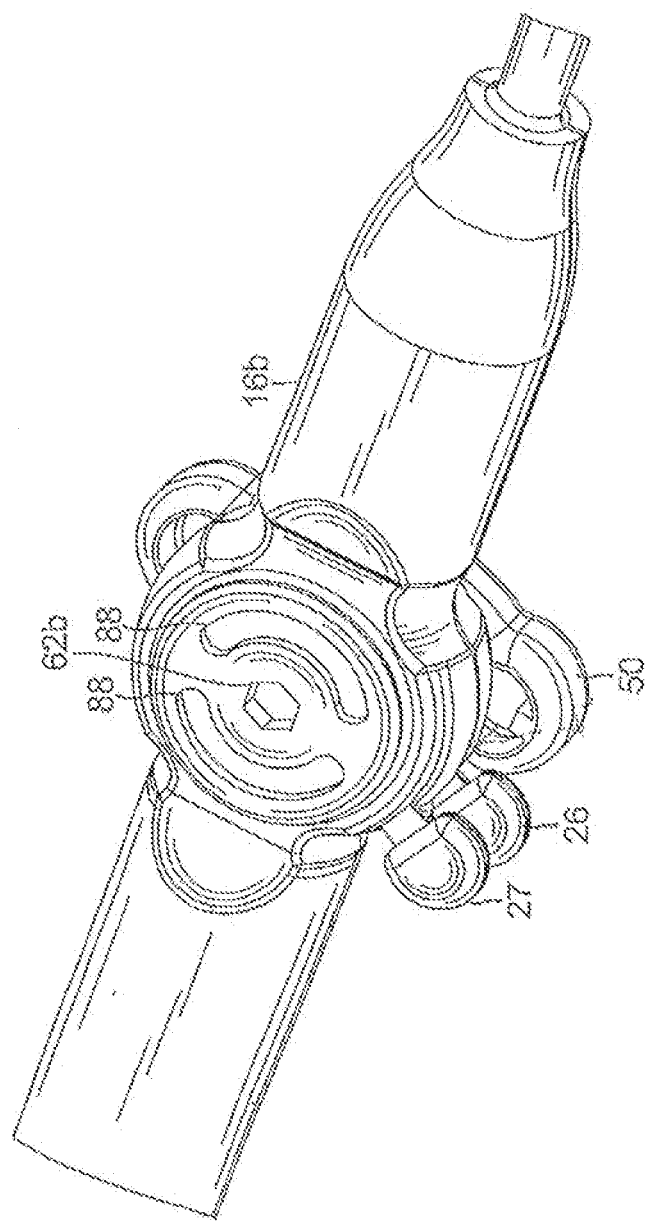
FIG. 13 is a perspective view of an outer surface of an embodiment of a second control handle housing half.

With reference to FIGS. 1A and 1B, mounted on the radial bearing formation 61b of control handle housing half 16b and opposing the deflection knob 50 is a tension adjustment assembly 43 which includes a tension adjustment dial 80 that is coupled to and indirectly engaged with the pulley arm 52 by various mechanisms and parts. The dial 80 allows a user to adjust the ease with which the deflection knob 50 can be rotated. In the illustrated embodiment, the tension adjustment assembly 43 includes the dial 80 (FIG. 12), a locking plate 82 (FIG. 12), a tension cap screw 83, a retaining nut 84 and a washer 85. The nut 84 has an end 87 (FIG. 14) with a polygonal (e.g., hexagonal) shape that locks with the through-opening 62b to prevent rotation of the nut 84 when the tension cap screw 83 is rotated to adjust the compression load applied to assembly 43 against the washer 85. The dial 80 has two prongs 86 (FIG. 12) that extend through the locking plate 82 and into guiding grooves 88 (FIG. 13) formed on an outer surface of the housing half 16b which limits the range of rotation of the dial 80. A user rotates the dial 80 to adjust the tightness or tension of the rotational movement of deflection arm 50 by effectively compressing or releasing the pulley arm 52 against the washer 85 (e.g., a Belleville type) and the control handle housing half 16b. A suitable deflection assembly is described in U.S. Pat. No. 7,377,906, the entire disclosure of which is hereby incorporated by reference.

In accordance with a feature of the present invention, the control handle includes the second actuator 26 for controlling an additional puller wire (or contraction wire) 35a. With reference to FIGS. 1A, 1B and 15, the second actuator 26 is mounted on the radial bearing formation 61a between the main body of the pulley arm 52 and the control handle housing half 16a, adjacent the deflection knob 50. The second actuator 26 has a disk-shaped body 90a with a center through-hole 92 through which the radial bearing formation 61a is inserted. The second actuator has an elongated tab 94b extending from a periphery of the disk-shaped body which extends through a through-slot 96a in the housing half 16a. An enlarged handle 98 is mounted on an end of the tab 94b to facilitate manipulation by the user. The actuator 26 is thus rotatable about the radial bearing formation 61a (and hence about the rotational axis 69) within a range as limited by a length of the through-slot 96a.

The puller wire 35a for controlling an additional feature also enters the control handle through the port 74. A raised center divider 100 is formed in the housing handle 16b to guide the puller wire toward the actuator 26. The puller wire wrapped around the radial bearing formation 61a and anchored to the body 90a. In the disclosed embodiment, a through-hole 102 is formed on the body 90a for receiving a proximal end of the puller wire 35a which is tied in a knot to anchor the proximal end to the body. A second through-hole 103 may be provided as an alternate anchor position for the puller wire 35a.

With reference to FIGS. 1A, 1B and 15, the third actuator 27 for controlling yet another additional puller wire 35b is mounted on the opposing radial bearing formation 61b between the main body of the pulley arm 52 and the control handle housing half 16b, adjacent the tension adjustment dial 80. The third actuator 27 and its puller wire 35b are similar in structure and function to the second actuator 26 and its puller wire 35a.

Thus, with either actuator 26 or 27, as the actuator is rotated about the rotational axis 69 in one direction, the respective puller wire is wrapped around the respective radial bearing formation and drawn proximally from its original position to actuate the respective feature. When the actuator is rotated in the opposite direction, the puller wire and the feature are released to assume their original positions.

It is further understood that additional disk actuators can be mounted on either of the radial bearing formation. Because each actuator is rotationally independent of the radial bearing formation on which it is mounted each actuator can be operated independently of the pulley arm and each other by the user to control a feature without affecting any other feature.

Figure 17:
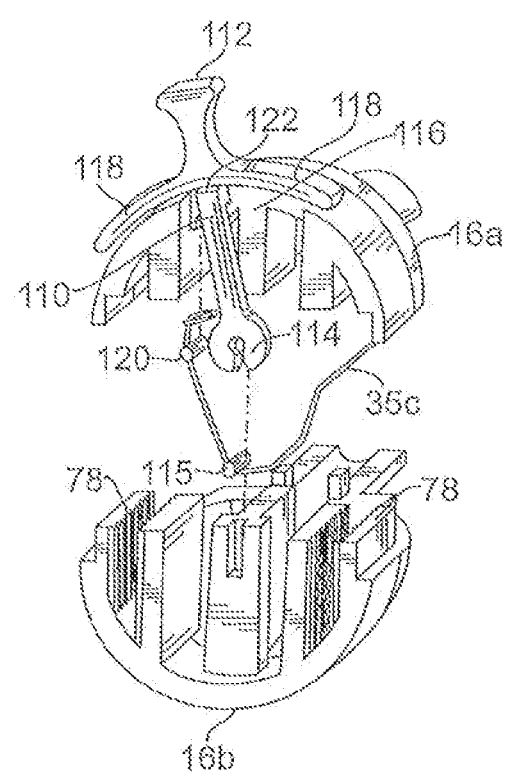
FIG. 17 is an exploded perspective view of the lever actuator of FIG. 15.

In accordance with a feature of the present invention, an additional lever actuator 28 is provided in the distal portion of the control handle. The actuator 28 is rotatable about an axis that is at least parallel, if not coaxial, with the longitudinal axis 64 of the control handle. In the illustrated embodiment of FIG. 17, the actuator has an elongated body 110 with an outer end 112 adapted for manipulation by the user for rotation at an inner end 114 about a longitudinal dowel pin 115 mounted in the control handle housing half 16b. The inner end 114 has a female snap-fit formation that rotatably engages the dowel pin 115. The outer end extends through a transverse through-slot 116 (FIG. 11) formed in the housing half 16a so that the outer end 112 is accessible to the user, with the range of rotation being limited by the length of the slot 116. The actuator 28 has a shroud portion 118 that extends transversely to the elongated body so that the actuator resembles a "t". The shroud portion 118 is outside of the control handle 16 and has a profile (e.g. curved) matching the profile of the housing half 16a to effectively seal the slot 116 and protect the interior of the control handle from exposure.

A puller wire 35c for controlling yet another additional feature also enters the control handle through the port. The puller wire is guided by the raised divider 100 and extends below the dowel pin 115 and around a longitudinal dowel pin 120 mounted off-set from the longitudinal axis of the dowel pin 115 in the control handle housing half 16a. A proximal end of the puller wire 35c is anchored to a junction 122 of the elongated body 110 and the shroud portion 118. Thus, when the user rotates the actuator 28 away from the dowel pin 120, the puller wire 35c is drawn proximally from its original position to actuate the feature. When the actuator is rotated toward the dowel pin, the puller wire and the feature are released to assume their original positions.

Figure 18:
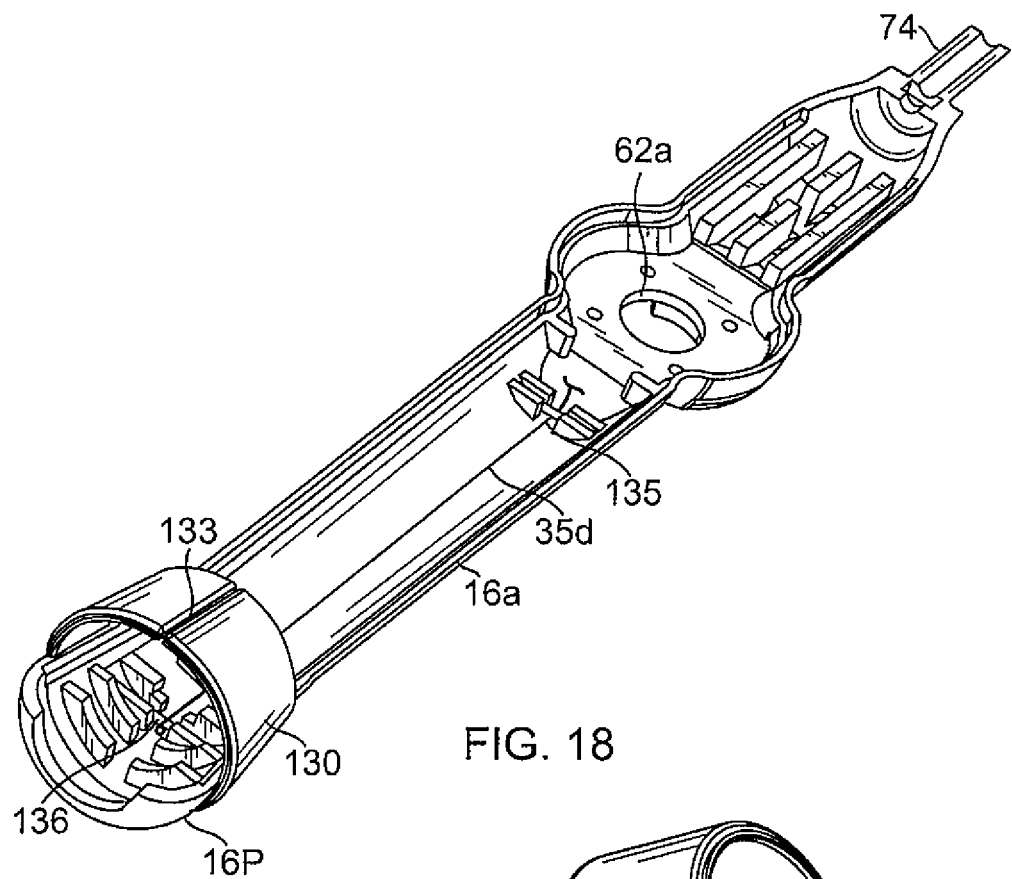
FIG. 18 is a perspective view of an inner surface of an embodiment of the first control handle housing half, with an embodiment of a ring actuator.
Figure 19:
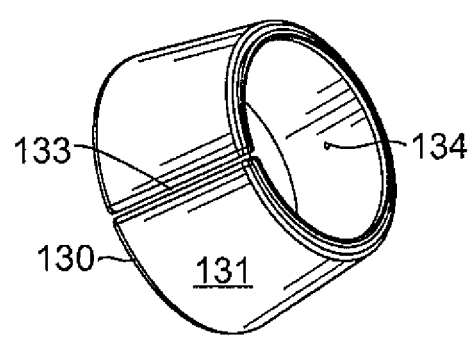
FIG. 19 is a perspective view of the ring actuator of FIG. 18.

In accordance with a feature of the present invention, the control handle 16 includes a fourth or ring actuator 130 for controlling another additional puller wire 35d. In the illustrated embodiment of FIGS. 11 and 18, the fourth actuator 130 is mounted on the proximal portion 16P of the control handle and has a rotational axis coaxial with longitudinal axis 64 of the control handle. In the illustrated embodiment, the actuator 130 has a generally cylindrical body or ring 131 (e.g., a frusto-conical configuration) that is mounted outside of the control handle in a circumferential relationship therewith. A circular band of outer surface of the housing halves 16a and 16b under the ring 131 is depressed relative to the surrounding outer surface to form a nest so that the ring is nested in its longitudinal position along the control handle while being allowed circumferential rotation relative to the control handle. The body has a slit 133 extending in a direction along the longitudinal axis so that the body can be mounted on the control handle by slipping it over the proximal end of the control handle. An aperture 134 is formed in the body diametrically opposite of the slit.

The puller wire 35d for controlling a further additional feature enters the control handle through the port 74. The puller wire 35d extends along in a longitudinal groove (not shown) formed in the inner surface of the housing half 16a from the port 74 and around the opening 62a to bypass the pulley arm 52. The puller wire 35d is then guided in the distal portion 16D of the control handle 16 by a proximal transverse dowel pin 135 and a distal transverse dowel pin 136 mounted in the housing half 16a and passes through the aperture 134 in the housing half 16a to reach the fourth actuator 130 where a proximal end of the puller wire is anchored to the ring actuator 130. A proximal portion of the puller wire 35d is received in a groove with a predetermined pattern (e.g., spiral) which is filled with glue or the like to anchor the proximal end to the ring actuator.

As a user rotates the actuator 130 in one direction, the puller wire 35d is drawn proximally through the aperture 134 to wrap around the nest between the control handle 16 and the ring 131 to actuate a feature. When the actuator 130 is rotated in the opposite direction, the puller wire 35d and the feature are released to return to their original positions. An O-ring (not shown) may be provided in the nest between the control handle 16 and the ring 131 to provide friction so as to render the actuator 130 self-holding.

In use, a suitable guiding sheath is inserted into the patient with its distal end positioned at a desired location. An example of a suitable guiding sheath for use in connection with the present invention is the Preface™ Braiding Guiding Sheath, commercially available from Biosense Webster, Inc. (Diamond Bar, Calif.). The distal end of the sheath is guided into one of the chamber, for example, the atria. A catheter in accordance with an embodiment of the present invention is fed through the guiding sheath until its distal end extends out of the distal end of the guiding sheath. As the catheter is fed through the guiding sheath, the distal assembly 17 is straightened to fit through the sheath. Once the distal end of the catheter is positioned at the desired location, the guiding sheath is pulled proximally, allowing the deflectable intermediate section 14 and distal assembly 17 to extend outside the sheath, and the distal assembly 17 returns to its original shape due to its shape-memory.

The user may then manipulate the deflection 50 to deflect intermediate section 14 Turning the deflection knob 50 in one direction deflects the intermediate section 14 to that direction. Turning the deflection 50 in the opposite direction deflects the intermediate section 14 to that opposite direction. The user may then adjust the generally circular main region 39 of the distal assembly 17 by rotating the first actuator 26 in one direction or another to fit a pulmonary vein or other tubular structure. In the disclosed embodiment, by rotating the dial in one direction, the contraction wire 35 is drawn proximally to tighten and decrease the diameter of the generally circular region 39 and by rotating the dial in the other direction, the third puller or contraction wire 35a is loosened to release the generally circular region 39 to its original diameter. Preferably at least about 50%, more preferably at least about 70%, and still more preferably at least about 80% of the circumference of the generally circular main region is in contact with a circumference inside the tubular region. The circular arrangement of the electrodes on the generally circular portion 39 permits measurement of the electrical activity at that circumference of the tubular structure so that ectopic beats between the electrodes can be identified. The size of the generally circular main region 39 permits measurement of electrical activity along a diameter of a pulmonary vein or other tubular structure of or near the heart because the circular main region has a diameter generally corresponding to that of a pulmonary vein or other tubular structure. Because the first actuator 26 and the deflection knob 50 are not rotationally coupled, each can be controlled independently of the other.

In accordance with a feature of the present invention, the first and second actuators are advantageously of designs that allow them to be added to existing control handles incorporating the pulley arm 52 without significant modifications to the structure of the control handle or interference with its function and operation. Likewise, the third and fourth actuators can be readily incorporated in existing control handles.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. For example, the catheter can be adapted such that the third puller wire advances and retracts another component such as a guide wire or a needle. As understood by one of ordinary skill in the art, the drawings are not necessarily to scale. Accordingly, the foregoing description should not be read as pertaining only to the precise structures described and illustrated in the accompanying drawings, but rather should be read consistent with and as support to the following claims which are to have their fullest and fair scope.

What is claimed is:
1. An electrophysiological catheter, comprising:
an elongated catheter body;
a distal section distal of the catheter body;
a control handle; and
a plurality of puller wires extending from the control handle and through at least the elongated catheter body, wherein the control handle comprises:
 a housing;
 a deflection assembly comprising:
  a deflection actuator adapted for rotation by the user;
  a pulley arm adapted for rotation about a rotational axis in response to rotation of the deflection actuator, at least a first of the puller wires coupled to the pulley arm, wherein rotation of the pulley arm actuates the at least first puller wire;
 a disk actuator adapted for rotation about the rotational axis by the user; and
 a second of the puller wires coupled to the disk actuator, wherein rotation of the disk actuator actuates the second puller wire to manipulate the distal section, wherein the pulley arm has a radial bearing formation defining the rotational axis, and the disk actuator is positioned on the radial bearing formation and adapted to wrap the second puller wire on the radial bearing formation when the disk actuator is rotated by the user, the disk actuator and the pulley arm being rotationally independent of each other.

2. A catheter of claim 1, the housing has an opening and the disk actuator has a tab extending through the opening to outside of the housing.

3. A catheter of claim 1, the pulley arm has a main body and the disk actuator is positioned between the main body and the housing of the control handle.

4. The electrophysiological catheter according to claim 1, further comprising:
   a lever actuator adapted for rotation about a second rotational axis by the user, the second rotational axis being generally parallel with the longitudinal axis of the control handle, a third of the puller wires being coupled to the lever actuator and rotation of the lever actuator actuates the third puller wire to manipulate the distal section,
   wherein the lever actuator and the pulley arm are rotationally independent of each other.

5. An electrophysiological catheter of claim 4, wherein the housing has an opening and the lever actuator has an end extending through the opening to outside the housing.

6. An electrophysiological catheter of claim 4, wherein the lever actuator has a shroud portion adapted to cover the opening.

7. The electrophysiological catheter according to claim 1, further comprising:
   a ring actuator mounted on the control handle and adapted for rotation about the longitudinal axis of the control handle, a third of the puller wires being coupled to the ring actuator and rotation of the ring actuator actuates the third puller wire to manipulate the distal section,
   wherein the ring actuator and the pulley arm are rotationally independent of each other.

8. An electrophysiological catheter of claim 7, wherein rotation of the ring actuator wraps the second puller wire around the control handle.

9. An electrophysiological catheter of claim 7, wherein the housing has an opening and a proximal portion of the second puller wire extends through the opening and is anchored to the ring actuator.

* * * * *